United States Patent

Occelli

[11] 4,143,055
[45] Mar. 6, 1979

[54] 2,4,6-TRISUBSTITUTED-2,3-DIHYDRO-BENZOFURAN DERIVATIVES

[75] Inventor: Emilio Occelli, Parabiago, Italy

[73] Assignee: Gruppo Lepetit S.p.A., Milan, Italy

[21] Appl. No.: 890,158

[22] Filed: Mar. 27, 1978

[51] Int. Cl.² .................................................. C07D 307/79
[52] U.S. Cl. .......................... 260/346.73; 260/346.22; 424/285
[58] Field of Search ...................... 260/346.22, 346.73

[56] References Cited

PUBLICATIONS

Wahab et al., J. fur Praktische Chemie, vol. 314 (No. 2), 1972, pp. 213–219.
Royer et al., Bull. Soc. Chim. Fr., (1967) pp. 915–922.
Ramachandran et al., J. of Organic Chemistry, vol. 28, (1963) pp. 398–403.
Epstein et al., J. of Organic Chemistry, vol. 30 (1965) pp. 1246–1247.

*Primary Examiner*—Henry R. Jiles
*Assistant Examiner*—Bernard Dentz
*Attorney, Agent, or Firm*—James W. Ambrosius

[57] ABSTRACT

New 2,4,6-trisubstituted-2,3-dihydro-benzofuran derivatives of the following general formula

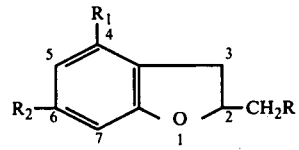

wherein R is selected from hydrogen or methyl; one of $R_1$ and $R_2$ represents hydroxy, $(C_{1-4})$alkoxy or $(C_{2-4})$alkanoyloxy, and the other one is selected from cyano, carboxy, carbo$(C_{1-4})$alkoxy, carbamoyl and a $-NR_3R_4$ group, wherein $R_3$ and $R_4$ independently represent hydrogen $(C_{1-4})$alkyl, $(C_{2-4})$alkanoyl, carbo$(C_{1-4})$alkoxy, carbobenzyloxy, carbamoyl, mono- and di-$(C_{1-4})$alkylamino-$(C_{1-4})$alkyl, benzenesulfonyl, toluenesulfonyl, $(C_{1-4})$alkylsulfonyl or phenacylsulfonyl; and salts therewith of pharmaceutically acceptable acids. The compounds have antinflammatory, analgesic and antipyretic utility.

4 Claims, No Drawings

2,4,6-TRISUBSTITUTED-2,3-DIHYDRO-BENZOFURAN DERIVATIVES

This is a division of application Ser. No. 514,987, filed Oct. 15, 1974, now U.S. Pat. No. 4,008,281.

BACKGROUND OF THE INVENTION 2,4,6-Trisubstituted-2,3-dihydro-benzofurans wherein the substituent at the 2-position is a methyl or an ethyl group represent a novel class of compounds. A few examples of 2,4,6-trisubstituted-benzofurans (the benzofuran skeleton has the following general formula:

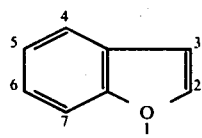

) are known, see for instance A. Wahhab, J. Prakt. Chem. 314, 213, 1972. Other benzofurans variously substituted at one or more of the possible positions are described in Bull. Soc. Chim. Fr., page 915, 1967, J. Org. Chem., 28, 398, 1963 and J. Org. Chem., 30, 1246, 1965.

SUMMARY OF THE INVENTION

The present invention is concerned with new 2,4,6-trisubstituted-2,3-dihydro-benzofuran derivatives of the following general formula

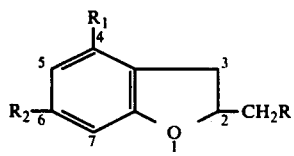

wherein R is selected from hydrogen or methyl; one of $R_1$ and $R_2$ represents hydroxy, $(C_{1-4})$alkoxy or $(C_{2-4})$alkanoyloxy, and the other one is selected from cyano, carbo$(C_{1-4})$alkoxy, carbamoyl and a —$NR_3R_4$ group, wherein $R_3$ and $R_4$ independently represent hydrogen, $(C_{1-4})$alkyl, $(C_{2-4})$alkanoyl, carbo$(C_{1-4})$alkoxy, carbobenzyloxy, carbamoyl, mono- and di-$(C_{1-4})$alkylamino-$(C_{1-4})$alkyl, benzenesulfonyl, toluenesulfonyl, $(C_{1-4})$alkylsulfonyl or phenacylsulfonyl; and salts therewith of pharmaceutically acceptable acids. The compounds possess antinflammatory, analgesic and antipyretic utility. The expression "$(C_{1-4})$alkyl" as used herein identifies alkyl radicals selected from methyl, ethyl, propyl, isopropyl, butyl, sec-butyl and tert-butyl; the term "$(C_{1-4})$alkoxy" designates alkoxy groups selected from methoxy, ethoxy, propoxy, isopropoxy, butoxy, sec-butoxy and tert-butoxy; the term "$(C_{2-4})$alkanoyloxy" refers to alkanoyloxy groups selected from acetyloxy, propionyloxy or butyryloxy; the term "lower $(C_{2-4})$alkanoyl" identifies alkanoyl radicals selected from acetyl, propionyl and butyryl. A preferred group of compounds comprises those compounds of formula I wherein R stands for hydrogen or methyl, one of $R_1$ and $R_2$ represents hydroxy, $(C_{1-4})$alkoxy as above defined or $(C_{2-4})$aliphatic alkanoyloxy as above defined, and the other one represents the group —$NR_3R_4$ wherein $R_3$ and $R_4$ each independently represents hydrogen or a $(C_{1-4})$alkyl group as above defined; and salts therewith of pharmaceutically acceptable acids. A most preferred group of compounds comprises those compounds of formula I wherein R is a hydrogen atom, one of $R_1$ and $R_2$ is a $(C_{1-4})$alkoxy group as above defined and the other one is the group —$NR_3R_4$ wherein $R_3$ and $R_4$ each independently represent hydrogen or $(C_{1-4})$alkyl as above defined; and salts therewith of pharmaceutically acceptable acids. Acids especially suitable for the formation of therapeutically useful salts are both organic and inorganic. Such acids are, for example, aliphatic or aromatic carboxylic acids, e.g. formic, acetic, succinic, oxalic, malic, tartaric, citric, ascorbic, benzoic and salicylic acid and mineral acids, e.g. hydrochloric, hydrobromic, sulfuric, phosphoric or perchloric acid. The compounds of this invention are prepared according to methods which involve, as the first step, formation of the basic 2,3-dihydrobenzofuran skeleton through cyclization of a compound of formula II

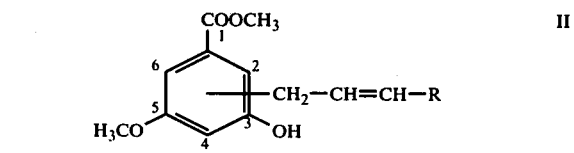

wherein R is defined as above. For the invention purposes, the radical —$CH_2$—$CH$=$CH$—R must be located either in the position 2 or in the position 4. Thus, when R represents hydrogen, the compound of formula II is an o-allylphenol derivative, when R is methyl, the compound of formula II is an o-crotylphenol derivative.

Depending on the position of the allyl or crotyl group on the benzene ring, cyclization to 2,3-dihydrobenzofurans is achieved through thermal or acid induced ring closure as summarized in the following schemes:

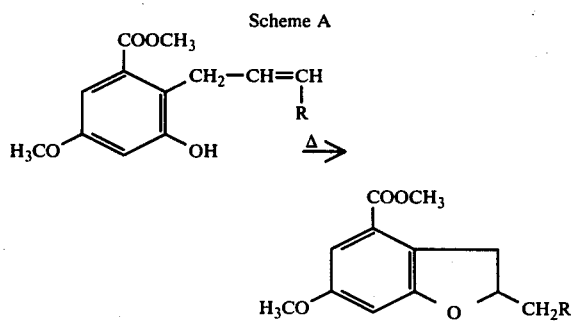

Scheme A

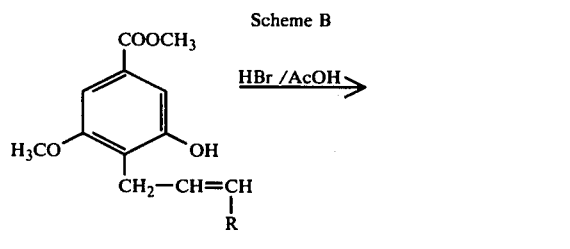

Scheme B

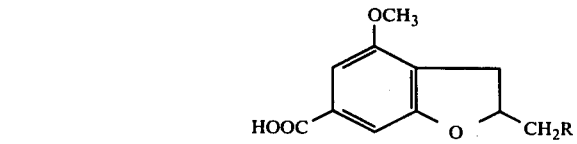

In the actual practice, cyclization of 2-allyl- or 2-crotyl-3-hydroxy-5-methoxybenzoic acid methyl esters according to Scheme A is performed by heating the starting material in an inert atmosphere, e.g. nitrogen or carbon dioxide atmosphere, to a temperature ranging from about 200° C. to about 280° C. for about 2–4 hours. The cyclized compound is then receovered according to the usual procedures which comprise dissolution of the cooled reaction mass in an aqueous alkaline solution, extraction with a water-immixable organic solvent, evaporation of the organic phase and purification of the product by vacuum distillation or column chromatography. Alternatively, this reaction can be carried out in a neutral or basic high-boiling organic solvent, heating the obtained reaction mixture to the reflux temperature for 2–6 hours.

At the end of this time the solvent is evaporated and the cyclization product is recovered as described above.

According to scheme B above the acid-induced cyclization of 4-allyl- or 4-crotyl-3-hydroxy-5-methoxybenzoic acid methyl esters is carried out by dissolving the starting material in acetic acid and subsequently adding hydrobromic acid.

The reaction may be performed at room temperature, however it is generally preferred to heat or even reflux the obtained reaction mixture in order to speed up the reaction which can be completed in 1–4 hours. Separation and purification of the obtained 2,3-dihydrobenzofurans is achieved according to the usual procedures, bearing in mind that the acidic reaction conditions afford the hydrolysis of the carbomethoxy group. It has also been found that, when the reaction time is prolonged up to 7–10 hours, also the hydrolysis of the methoxy group to hydroxy takes place.

The starting materials of formula II can be easily prepared by Claisen rearrangement of allylphenylethers of formula III

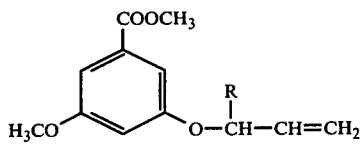

wherein R is hydrogen or methyl, performed as described in Tarbell in Organic Reactions, vol. II, New York, 1944, i.e., by heating the allylphenyl ether in the absence of any solvent to a temperature comprised between 180° and 220° C., or refluxing a solution of a compound of formula III in a basic or neutral high-boiling organic solvent.

Suitable solvents which may be employed comprise N,N-dimethylaniline, N,N-diethylaniline, paraffin oil, tetralin and kerosine. The rearrangement is preferably carried out in an inert atmosphere. Recovery of the obtained isomers is achieved according to the usual procedures taking advantage of the different solubilities of the corresponding carboxylic acids, obtained by alkaline hydrolysis, in aqueous solutions.

Alternatively, the two isomers can be precipitated as a mixture and separated by column chromatography. Usual esterification procedures afford the desired products of formula II Pursuant to the procedures outlined in schemes A and B, compounds of formula I are obtained wherein R stands for hydrogen or methyl, one of $R_1$ and $R_2$ is a methoxy radical and the other one is a carboxy or carbomethoxy group.

When other compounds of formula I are desired, then the corresponding groups have to be introduced by obvious chemical modifications, which are entirely familiar to an average technician. Thus, the alkaline hydrolysis of the 4-positioned carbomethoxy substituent leads to the corresponding carboxy group which in turn, as well as the carboxy group at the 6-position formed in the acid-induced cyclization, may be reacted with a $(C_{1-4})$alkanol in the presence of a strong acidic medium to yield the desired 4- or 6-carbo($C_{1-4}$)alkoxy derivatives.

The carboxy group at the 4- or 6-position may undergo other chemical modifications. For convenience purposes, it it first transformed into the more reactive —COhal group, wherein hal stands for a halogen atom, preferably chloro or bromo, which may in turn be converted into the corresponding —$CON_3$ group by reaction with $NaN_3$.

Alternatively, the —COhal group is transformed by ammonolysis into the corresponding amide which may be dehydrated, thus giving compounds of formula I wherein $R_1$ or $R_2$ is cyano.

The benzofurans bearing the —$CON_3$ group at the 4- or 6-position, prepared as described above, are intermediates for preparing other compounds falling within the scope of the general formula.

Thus, the thermal decomposition of the —$CON_3$ group affords compounds of formula I wherein $R_1$ or $R_2$ represent amino i.e., the group —$NR_3R_4$ in which $R_3$ and $R_4$ are hydrogen whereas, if the decomposition takes place in the presence of a $(C_{1-4})$alkanol or benzyl alcohol, compounds of formula I are obtained wherein $R_1$ or $R_2$ represent a carbo($C_{1-4}$)alkoxyamino or carbobenzyloxyamino radical. From these compounds, by means of a simple reductive step, the compounds where $R_1$ or $R_2$ represent methylamino are easily prepared. Among the reducing agents, lithium aluminum hydride is the most preferred one.

Also the substituents $R_3$ and $R_4$ different from hydrogen are introduced by means of known procedures by reacting the corresponding 4- or 6-unsubstituted amino derivatives with appropriate reactants.

Thus, for instance, reaction with an alkylating agent, such as $(C_{1-4})$alkyl halides or $(C_{1-4})$alkyl sulfates, affords compounds wherein $R_3$ or $R_4$ or both are $(C_{1-4})$alkyl groups. Compounds wherein $R_3$ or/and $R_4$ represent a $(C_{2-4})$alkanoyl radical are obtained by reacting the corresponding compounds wherein $R_3$ or/and $R_4$ are hydrogen with halides or anhydrides of $(C_{2-4})$aliphatic acids. Carbo($C_{1-4}$)alkoxy and carbobenzyloxy amino groups are obtained by reaction with corresponding $(C_{1-4})$alkyl and benzyl carbonates.

They may in turn be converted into the 4- or 6-methylamino derivatives as outlined above. The benzenesulfonyl, toluenesulfonyl, $(C_{1-4})$alkylsulfonyl and phenacylsulfonyl groups are conveniently introduced by reaction with benzenesulfonyl-, toluenesulfonyl-, $(C_{1-4})$alkylsulfonyl- and phenacylsulfonyl halides respectively, whereas the carbamoyl group may be introduced by reacting the unsubstituted amino derivative with an alkali isocyanate in an acidic medium.

An useful route to the compounds wherein one of $R_1$ and $R_2$ is a $(C_{2-4})$alkylamino group is represented by the reduction of the $(C_{2-4})$acyl substituents of the amino group.

Finally, also the corresponding 4- or 6-positioned methoxy group may be transformed by known chemical reactions into another group falling within the meanings given for said substituent: demethylation may be done by refluxing the compound with HBr/AcOH mixtures or alternatively refluxing a $CS_2$ or nitrobenzene solution of the compound with anhydrous $AlCl_3$ and decomposing the obtained aluminum complex with water. Reaction of the thus obtained hydroxy derivative with ($C_{2-4}$)alkyl sulfates in strongly alkaline medium affords the corresponding ($C_{2-4}$)alkoxy derivatives, whereas the 4- or 6-positioned ($C_{2-4}$)alkanoyloxy group may be obtained through reaction with a suitably selected ($C_{2-4}$) aliphatic acyl halide or anhydride in acidic conditions.

It is intended that alternative methods which can suitably be employed for transforming a pre-existing radical into an other falling within the given meanings, although not specifically disclosed, are to be considered within the scope of the present invention.

As stated above the compounds of the present invention possess antinflammatory, analgesic and antipyretic utility. They also possess a low toxicity, since the $LD_{50}$ values are never lower than 1000 mg/kg orally in mice and higher than 2000 mg/kg orally in rats. The toxicities were determined according to Lichtfield and Wilcoxon, Journ. Pharm. Expt. Ther., 96, 99, 1949.

The antiinflammatory activity was ascertained by means of several testing methods; in one, the ability of the compounds of the invention to reduce the edema induced in the rat paw by injection of carrageenin was evaluated and the test was performed according to the methodology described by C. A. Winter et al. in Proc. Soc. Exptl. Biol. Med. 111, 544, (1962). In another it was investigated the reduction by the test compounds of the weight of the granuloma formed on a cotton pellet implanted subcutaneously in a rat, following the method described by Meier et al. in Experientia 6, 469, (1950).

Representative experiments have shown that the compounds of Example 11, namely 2,3-dihydro-6-methoxy-N,2-dimethyl-4-benzofuranamine causes a reduction of the carrageenin induced edema of around 70 percent over the controls even when it is administered at an absolutely safe dosage i.e., around 1/5 of its $LD_{50}$. In the granuloma cotton pellet test the same compound at the same dosage reduces the weight of the granuloma of more than 40 percent again over the controls.

However, the most important pharmacological aspect of the compounds of the present invention is that they are effective also in the adjuvant induced arthritis test in rats. Said test is absolutely meaningful in that adjuvant arthritis is one of the best pharmacological parameters with which a pharmacologist can investigate compounds as to their possible antinflammatory activity, owing to the parallelism of effects existing between it and some articulation diseases observed in humans (see Pearson, C. M., Arthritis and allied conditions, page 119, Lea and Febiger Publ., 1967 and Pearson, C. M., J. Chronic Diseases, 16, 863, 1963).

The adjuvant induced arthritis test was performed as described by B. B. Newbould in Brit. Jour. Pharmacol., 21, 127, (1963). The measure of effectiveness of the compounds in this test is given by their ability in reducing the volume of the hind paws of the laboratory animals. In still another representative experiment, the compound of Example 11 proved to be significantly more active in the adjuvant induced arthritis test than acetylsalicylic acid, which is one of the most effective and widely employed antirheumatic drug. The obtained results, which are summarized in the following table, were obtained by testing the compounds at a dosage corresponding to 1/5 of their $LD_{50}$.

TABLE

| Compound | $LD_{50}$ mg/kg rats p.o. | Dose mg/kg rats p.o. | % reduction of the volume of the hind paws over the controls |
|---|---|---|---|
| 2,3-dihydro-6-methoxy-N,2-dimethyl-4-benzofuranamine | 2800 | 200 | 36 |
| acetylsalicylic acid | 1400 | 200 | 25 |

These favorable characteristics are coupled also with interesting analgesic and antipyretic properties which were investigated according to the methods described by Randall et al. in Arch. Int. Pharmacodyn. 111, 409, (1957) and by Builler et al. in J. Pharm. Pharmacol. 9, 128, (1957), respectively. It is finally to be noted that the new 2,3-dihydro-benzofuran derivatives which are the object of the present invention display a very low ulcerogenic activity which is several times lesser than the one observed with other know and therapeutically used antiinflammatory substances. The ulcerogenic action was determined according to Thuillier et al. Chim. Ther. 3, 51, (1968).

The following examples illustrate the process of the invention and describe in detail some compounds of general formula I without limiting the scope of the invention.

EXAMPLE 1

2,3-dihydro-6-methoxy-2-methyl-4-benzofurancarboxylic acid methyl ester 2-allyl-3-hydroxy-5-methoxybenzoic acid methyl ester is heated under nitrogen atmosphere to 260° C. for about 3 hours. Upon cooling, the reaction mass is dissolved in a small amount of 20%KOH and the aqueous alkaline solution is then extracted with ethyl ether. The organic phase is evaporated and the crude residue affords the title compound in 45% yield. B.p./0.3 mmHg 136°–38° C.

EXAMPLE 2

2,3-dihydro-4-methoxy-2-methyl-6-benzofurancarboxylic acid 1 gram of 4-allyl-3-hydroxy-5-methoxybenzoic acid methyl ester in 5 cc of glacial acetic acid and 1.5 cc of 48%HBR is refluxed for 3 hours. After this time the mixture is concentrated to dryness and the crude residue is dissolved in an aqueous alkali solution. 0.3 grams of dimethyl sulfate are added to the resulting solution which is refluxed for two additional hours. The compound of the title which precipitates upon acidification of the cooled reaction mixture is recrystallized from ethyl ether-petroleum ether. Yield 60%. M.p. 180°–182° C.

EXAMPLE 3

2,3-dihydro-4-hydroxy-2-methyl-6-benzofurancarboxylic acid

A mixture of 30 grams of 4-allyl-3-hydroxy-5-methoxybenzoic acid, 150 cc of glacial acetic acid and 45 cc of 48%HBr is heated to the reflux temperature for 8 hours. After this time the reaction mixture is concentrated to dryness and the obtained residue, ground with water and filtered is crystallized from ethyl ether-petroleum ether. The product is obtained in a yield of 19.9 grams (71 percent of theoretical) and has a melting point of 181°–184° C.

EXAMPLE 4

2,3-dihydro-6-hydroxy-2-methyl-4-benzofurancarboxylic acid

To a solution of 35 grams of 2,3-dihydro-6-methoxy-2-methyl-4-benzofurancarboxylic acid methyl ester, prepared in Example 1, in 160 cc of acetic acid, 60 cc of 48%HBr are added and the resulting mixture is refluxed for 16 hours. After this time the reaction mixture is concentrated to dryness and the residue is dissolved in concentrated NaOH. The obtained solution, heated in a hot water-bath for 2 hours, is then cooled, acidified with concentrated HCl and extracted with ether. Evaporation of the ether extract affords a crude residue which is purified by column chromatography using a mixture $CHCl_3$-MeOH as the eluting system wherein the percentage of MeOH is gradually increased. The compound of the title, recovered from the last fractions ($CHCl_3$ + 3% MeOH), is then crystallized from ethyl ether-petroelum ether. Yield 14.2 g (47 percent of theoretical). M.p. 225°–27° C.

EXAMPLE 5

6-ethoxy-2,3-dihydro-2-methyl-4-benzofurancarboxylic acid 6.9 grams of the compound prepared in the preceding example are dissolved in 25 cc of 22%NaOH and the resulting solution maintained at 30° C. during the dropwise addition of 9 cc of diethyl sulfate, is then refluxed for 2 hours. After adding 2 cc of concentrated NaOH, heating is continued for two additional hours.

At the end of this time the mixture is cooled, acidified with concentrated HCl and filtered.

The solid recovered on filter is dissolved in ethyl ether and the obtained solution, dried over $Na_2SO_4$, is then concentrated to a small volume. The solid which precipitates upon addition of petroleum ether is recrystallized from ethyl ether yielding 5.9 grams (75% of theoretical) of 6-ethoxy-2,3-dihydro-2-methyl-4-benzofurancarboxylic acid which melts at 155°–157° C.

EXAMPLE 6

(6-ethoxy-2,3-dihydro-2-methyl-4-benzofuranyl)carbamic acid ethyl ester (a) A solution consisting of 5.7 grams of 6-ethoxy-2,3-dihydro-2-methyl-4-benzofurancarboxylic acid, prepared in example 5, 3.7 cc of $SOCl_2$, a few drops of N,N-dimethylformamide and 60 cc of anhydrous benzene, is gently refluxed for 4 hours. At the end of this time the reaction mixture is concentrated to dryness and the obtained residue, dissolved in 65 cc of acetone, is cooled to 5° C. while a solution of 2.8 grams of sodium azide in 8 cc of water is gradually added under stirring. Stirring, at the same temperature, is prolonged for an additional hour then the reaction mixture is poured into ice-water and extracted with ether. Evaporation of the oganic phase affords an oily residue which is the azide of the starting carboxylic acid.

(b) This oily residue, dissolved in 60 cc of anhydrous xylene, is gradually heated up to 120° C. and maintained at this temperature for 30 minutes. After this time 10 cc of EtOH are added drop by drop to the reaction mixture which is then refluxed for 3 hours. The residue obtained by evaporating the solvent is finally crystallized from ethyl ether yielding 5.3 grams (93 percent of theoretical) of the compound of the title. M.p. 64° C.

EXAMPLE 7

6-ethoxy-2,3-dihydro-N2-dimethyl-4-benzofuranamine hydrochloride

A solution of 4.1 grams of the compound prepared in the preceding example in 30 cc of anhydrous benzene is gradually added to a suspension of $LiAlH_4$ (1 gram) in anhydrous ethyl ether (35 cc). The obtained reaction mixture, refluxed for 6 hours, is then cooled and the aluminum complex is decomposed by addition of 3 cc of water. After stirring at room temperature for 30 minutes the inorganic salts are discarded by filtration, the filtrate is evaporated and HCl is bubbled in a solution of the obtained residue in ethyl ether. The precipitate which forms is recovered on filter and recrystallized from ethyl alcohol-ethyl ether yielding 3 grams (80 percent of theoretical) of the compound of the title which melts at 173°–175° C.

EXAMPLE 8

2,3-dihydro-6-methoxy-2-methyl-4-benzofurancarboxylic acid

To a stirred mixture of 158 grams of 2,3-dihydro-6-methoxy-2-methyl-4-benzofurancarboxylic acid methyl ester and 88.5 grams of flake sodium hydroxide in 320 cc of water, ethanol is gradually added until a clear solution is obtained.

The reaction mixture is allowed to stand at room temperature for about five hours then the solvent is evaporated under reduced pressure and the obtained residue, taken up with water and acidified with diluted HCl, is extracted with ether. By concentrating to dryness the organic phase and crystallizing the residue from ethyl ether on addition of petroleum ether, 106 grams (71.6 percent of theoretical) of the compound of the title are obtained. M.P. 153°–155° C.

EXAMPLE 9

2,3-dihydro-6-methoxy-2-methyl-4-benzofuranamine 70 cc of $SOCl_2$ are dripped at room temperature into a stirred solution of 106.8 grams of 2,3-dihydro-6-methoxy-2-methyl-4-benzofurancarboxylic acid in 840 cc of anhydrous benzene. When the addition is terminated the reaction mixture is heated to 80° C. for 5 hours and then concentrated to dryness. The thus obtained residue, consisting of the acyl chloride of the starting acid, is purified by crystallization from ethyl ether-petroleum ether and dissolved in 1370 cc of anhydrous acetone. To the resulting solution cooled under stirring to +5° C., 61.6 grams of $NaN_3$ dissolved in 180 cc of water are gradually added. The same temperature is maintained for an additional hour then the reaction mixture is poured into 4600 cc of distilled cold water. Extraction with ethyl ether and evaporation of the organic phase affords the crude azide of the starting carboxylic acid which is purified by crystallization from ethyl ether.

A solution of this intermediate in 100 cc of ethyl ether is gradually added under stirring to 600 cc of ethylene glycol heated in an oil-bath to 85° C. When the addition is terminated, the temperature is increased to 220° C. for 5 minutes then the reaction mixture is alkalized by means of an ethylene glycol solution of 98 grams of flake KOH and refluxed for 20 minutes. After cooling, the reaction mixture is poured into 1200 cc of distilled icy water, stirred for 10 minutes, acidified with concentrated HCl and, after 15 minutes, made basic again with concentrated NaOH. By extracting with ethyl ether, evaporating this organic extract and crystallizing the resulting residue from petroleum ether, 81 grams of the compound of the title are obtained. M.p. 59°–61° C. Overall yield, calculated on the starting carboxylic acid, 88.6%.

EXAMPLE 10

(2,3-dihydro-6-methoxy-2-methyl-4-benzofuranyl)carbamic acid ethyl ester 55.75 grams of ethylchlorocarbonate in 100 cc of anhydrous benzene are gradually added at 5° C. to a stirred solution of 81 grams of 2,3-dihydro-6-methoxy-2-methyl-4-benzofuranamine and 46 cc of triethylamine in 700 cc of anhydrous benzene. At the end of the addition, the reaction mixture is slightly warmed and stirring is continued, at room temperature, for 3 hours. After this time the reaction mixture is refluxed for two hours, then cooled, washed with water, dried over $Na_2SO_4$ and concentrated to dryness yielding 95.81 grams (83.5 percent of theoretical) of the compound of the title B.p./0.4 mmHg 172° C.

EXAMPLE 11

2,3-dihydro-6-methoxy-N,2-dimethyl-4-benzofuranamine 95.81 grams of (2,3-dihydro-6-methoxy-2-methyl-4-benzofuranyl)carbamic acid ethyl ester prepared in the foregoing example, are dissolved in 385 cc of anhydrous ethyl ether and the resulting solution is dripped into a stirred suspension of 21.01 grams of $LiAlH_4$ in 600 cc of anhydrous ethyl ether cooled to 0° C., then the obtained reaction mixture is refluxed for 5 hours. After cooling, 63 cc of cold distilled water are added to the reaction mixture and the inorganic salts which precipitate are discarded by filtration. The filtrate, dried over $Na_2SO_4$ is evaporated yielding an oily residue which purified by under vacuum distillation affords 34 grams of the compound of the title B.p./0.3 mmHg 137° C. This compound, which easily solidifies, melts at 53° C. (from ethyl ether-petroleum ether). The corresponding hydrochloride melts at 147° C.

EXAMPLE 12

N-(2,3-dihydro-6-methoxy-2-methyl-4-benzofuranyl)-propanamide

The compound of the title is prepared according to the procedure described in Example 10 by reacting the starting 2,3-dihydro-6-methoxy-2-methyl-4-benzofuranamine with propionyl chloride instead of ethylchlorocarbonate. M.p. 101°–02° C. (from ethyl ether). Yield 44 grams (75 percent of theoretical).

EXAMPLE 13

2,3-dihydro-6-methoxy-2-methyl-N-propyl-4-benzofuranamine

A solution of 3.2 grams of N-(2,3-dihydro-6-methoxy-2-methyl-4-benzofuranyl)propanamide, prepared in the foregoing example, in 30 cc of anhydrous benzene is gradually added into a suspension of 1.1 grams of $LiAlH_4$ in 30 cc of anhydrous ethyl ether at 0° C. and the resulting reaction mixture is heated to the reflux temperature for 6 hours. At the end of this time the temperature is decreased to 0° C. and the aluminum complex is decomposed by addition of 3.3 cc of water. After 30 minutes of stirring at room temperature, the inorganic salts are discarded by filtration and the filtrate, dried over $Na_2SO_4$, is concentrated to dryness. The under vacuum distillation of the obtained residue affords 2.8 grams (93 percent of theoretical) of the title compound. B.p./0.2 mmHg 140°–142° C. The corresponding hydrochloride prepared by treatment of the free base with HCl melts at 110°–111° C.

EXAMPLE 14

N-ethyl-2,3-dihydro-6-methoxy-2-methyl-4-benzofuranamine 3 grams of 2,3-dihydro-6-methoxy-2-methyl-4-benzofuranamine and 2.02 grams of triethylamine in 30 cc of anhydrous benzene are poured in a steel reaction vessel and added with 5 cc of ethyl bromide and trace amounts of potassium iodide.

The reaction vessel is sealed and heated in a oil-bath to 100° C. for 15 hours.

At the end of this time the reaction mixture is allowed to cool and then filtered. The filtrate is concentrated to dryness and an oily residue is obtained which on distillation under reduced pressure yields 1.1. grams of the desired product. B.p./0.5 mmHg 135° C.

EXAMPLE 15

N,N-diethyl-2,3-dihydro-6-methoxy-2-methyl-4-benzofuranamine

The alkylation reaction is carried out exactly as in the preceding example and the same procedures are followed up to the second filtration. Then, in order to recover the desired diethylamino derivative, the benzene filtrate containing the monoethylamino derivative is discarded whereas the remaining solid is taken up with water. The obtained solution is cooled, made basic by addition of 50% NaOH and thoroughly extracted with ethyl ether. The oily residue afforded by evaporating the organic phase is distilled under reduced pressure yielding 1.2 grams of N,N-diethyl-2,3-dihydro-6-methoxy-2-methyl-4-benzofuranamine. B.p./0.5 mmHg = 131° C.

EXAMPLE 16

N-(2,3-dihydro-6-methoxy-2-methyl-4-benzofuranyl)acetamide

This compound is prepared according to the procedures of example 10 by reacting 2,3-dihydro-6-methoxy-2-methyl-4-benzofuranamine with acetyl chloride. M.p. 104° C. (from isopropyl ether/ethyl alcohol).

EXAMPLE 17

N-(2,3-dihydro-6-methoxy-2-methyl-4-benzofuranyl)-diacetamide

A reaction mixture consisting of 2.4 grams of 2,3-dihydro-6-methoxy-2-methyl-4-benzofuranamine, 10 cc of acetic anhydride and one drop of pyridine is heated to 130°–140° C. for 90 minutes. After cooling and evaporating the excess of acetic anhydride, the residue is distilled under reduced pressure yielding 2.4 grams (69 percent of theoretical) of the compound of the title. B.p./0.4 mmHg 160° C. The distillate which solidifies is crystallized from ethyl ether-petroleum ether. M.p. 56°–57° C.

EXAMPLE 18

(2,3-dihydro-6-methoxy-2-methyl-4-benzofuranyl)-phenylacetamide

The compound of the title is prepared according to the procedures of example 10 starting from 2,3-dihydro-6-methoxy-2-methyl-4-benzofuranamine and benzoyl chloride. M.p. 148° C. (from isopropyl ether-ethyl alcohol).

EXAMPLE 19

N,N-diethyl-N'-(2,3-dihydro-6-methoxy-2-methyl-4-benzofuranyl)-1,2-ethanediamine dihydrochloride 2.80 grams of 2-diethylamino-ethyl chloride and traces of potassium jodide are added to a solution of 3 grams of 2,3-dihydro-6-methoxy-2-methyl-4-benzofuranamine and 2.02 grams of triethylamine in 50 cc of anhydrous toluene and the resulting reaction mixture is refluxed for 16 hours. After cooling and washing with water, the toluene phase is dried over $Na_2SO_4$ and then concentrated to dryness. Hydrochloric acid is added to an ether solution of the resulting oily residue until a solid precipitates then the mixture is cooled. The precipitate is recovered on filter and recrystallized from ethanol by addition of ethyl ether, yielding 3.55 grams of the title compound. M.p. 158°–159° C.

EXAMPLE 20

N-(2,3-dihydro-6-methoxy-2-methyl-4-benzofuranyl) urea

To a solution of 15.5 grams of 2,3-dihydro-6-methoxy-2-methyl-4-benzofuranamine and 10.5 grams of anhydrous pyridine in 100 cc of methylene chloride cooled to 0°–5° C., a solution of 24.5 grams of phenacylsulfonyl chloride in 80 cc of methylene chloride is added. When the dripping is terminated the reaction mixture is warmed to room temperature and stirred for 5 hours. At the end of this time the solution is washed with water, dried over sodium sulfate and concentrated to dryness. Crystallization of the resulting thick oil from ethyl alcohol-ethyl ether gives 16 grams of the compound of the title which melts at 143°–145° C.

EXAMPLE 21

N-(2,3-dihydro-6-methoxy-2-methyl-4-benzofuranyl)urea 2.5 grams of 2,3-dihydro-6-methoxy-2-methyl-4-benzofuranamine are dissolved in 16 cc of 0.1N HCl and upon gradual addition of 1.1 gram of sodium cyanate to the resulting solution a white crystalline solid precipitates. The reaction mixture is then heated in a water-bath and, after 90 minutes, cooled and filtered. By recrystallizing the obtained precipitate from ethyl alcohol 1.9 gram (61 percent of theoretical) of the desired product is obtained. M.p. 204°–06° C.

EXAMPLE 22

(2,3-dihydro-6-methoxy-2-methyl-4-benzofuranyl)carbamic acid phenylmethyl ester 0.65 grams of phenylmethylchlorocarbonate are dripped at 5° C. into a stirred mixture containing 0.7 grams of 2,3-dihydro-6-methoxy-2-methyl-4-benzofuranamine hydrochloride, 5 cc of 2N NaOH and 10 cc of chloroform. When the addition is terminated vigorous stirring is continued for one hour at the same temperature and for two hours at room temperature. Then the organic phase is separated, washed with water, dried over $Na_2SO_4$ and concentrated to dryness. The obtained residue crystallized twice from ethyl ether-petroleum ether yields 0.9 grams (88 percent of theoretical) of (2,3-dihydro-6-methoxy-2-methyl-4-benzofuranyl)carbamic acid phenylmethyl ester which melts at 82°–83° C.

EXAMPLE 23

N-(2,3-dihydro-6-methoxy-2-methyl-4-benzofuranyl)-N-methylpropanamide

The reaction is carried out as in example 10 by dripping propionyl chloride into a benzene solution of 2,3-dihydro-6-methoxy-N-2-dimethyl-4-benzofuranamine and triethylamine. Recovery of the crude end product is achieved by cooling the reaction mixture, previously refluxed for two hours, separating the obtained precipitate which, ground with benzene and filtered, is then discarded and finally concentrating the benzene filtrate to dryness. Distillation under reduced pressure of the resulting residue affords 2 grams (90 percent of theoretical) of pure compound. B.p./0.4 mmHg 140°–42° C.

EXAMPLE 24

(2,3-dihydro-4-methoxy-2-methyl-6-benzofuranyl)carbamic acid ethyl ester

A solution of 4.5 cc of $SOCl_2$ in 10 cc of anhydrous benzene is added drop by drop to 6.5 grams of 2,3-dihydro-4-methoxy-2-methyl-6-benzofurancarboxylic acid, prepared in example 2, suspended in 65 cc of anhydrous benzene and a few drops of N,N-dimethylformamide. The reaction mixture is gradually heated up to 70°–80° C. and stirred at the same temperature for 4 hours. Then the solvent is evaporated and the obtained thick oil is dissolved in 65 cc of acetone. 3,9 grams of $NaN_3$ in 15 cc of water are added into the resulting solution cooled to about 5° C. and stirring is continued at the same temperature for an additional hour.

At the end of this time the reaction mixture is poured into 400 cc of icy water and extracted twice with 100 cc of ethyl ether. The organic phase is evaporated and the residue redissolved in 150 cc of ethyl ether and dried over $Na_2SO_4$ is concentrated to a small volume. The solid which precipitates upon addition of petroleum ether is dissolved in 60 cc of anhydrous xylene and heated under stirring up to 120° C. After 30 minutes at this temperature, 10 cc of anhydrous ethanol are added and the mixture is heated in an oil-bath to 130° C. for 3 hours. At the end of this time the reaction mixture is concentrated to dryness and the resulting residue is distilled under reduced pressure wherein the fraction which at 0.4 mm Hg boils at 170°–80° C. is collected: crystallization from ethyl ether/petroleum ether of the solidified distillate gives 5 grams (78 percent of theoretical) of the compound of the title. M.p. 93°–94° C.

EXAMPLE 25

2,3-dihydro-4-methoxy-N,2-dimethyl-6-benzofuranamine

The compound of the title is prepared according to the procedures described in example 11 but starting from (2,3-dihydro-4-methoxy-2-methyl-6-benzofuranyl)carbamic acid ethyl ester. B.p./0.2 mmHg 130° C. Yield 94%.

The corresponding hydrochloride, crystallized from ethanol/ethyl ether melts at 157°–158° C.

EXAMPLE 26

2,3-dihydro-6-hydroxy-N,2-dimethyl-4-benzofuranamine 5 cc of 48% HBr are added to a solution of 5 grams of 2,3-dihydro-6-methoxy-N,2-dimethyl-4-benzofuranamine hydrochloride in 20 cc of acetic acid and the resulting mixture is refluxed for 16 hours. At the end of this time the solvent is evaporated off and the residue, taken up with sodium bicarbonate, is thoroughly extracted with ether. Evaporation of this organic phase, previously dried over $Na_2SO_4$, gives a crude residue which crystallized from ethyl ether-petroleum ether yields 3 grams of the desired end product. Yield 77 percent of theoretical. M.p. 126°–128° C.

EXAMPLE 27

6-acetoxy-2,3-dihydro-N,2-dimethyl-4-benzofuranamine hydrochloride 1.7 grams of the compound prepared in the foregoing example are added to 20 cc of ethanol containing 0.8 grams of HBr. Upon evaporation a tarry residue is obtained which is carefully dried in vacuo over $P_2O_5$. Then it is dissolved in 20 cc of $CF_3COOH$ and 1.4 grams of $CH_3COBr$ are gradually added into the resulting solution. After stirring for one hour a few drops of water are added and the reaction mixture is concentrated to dryness under reduced pressure by gently heating. The obtained residue is dissolved in a small amount of cold water and the solution made basic by addition of $NaHCO_3$ is thoroughly extracted with ethyl ether.

Evaporation of the ether phase and purification of the resulting residue by column chromatography using $CHCl_3$ + 1% acetone as the eluting system affords 6-acetoxy-2,3-dihydro-N,2-dimethyl-4-benzofuranamine whose hydrochloride crystallized from ethanol/ether melts at 159°–160° C. Yield 57 percent of theoretical.

Typical 2,4,6-Trisubstituted-2,3-dihydrobenzofurans which can be prepared by the procedures described in the above examples are as follows:

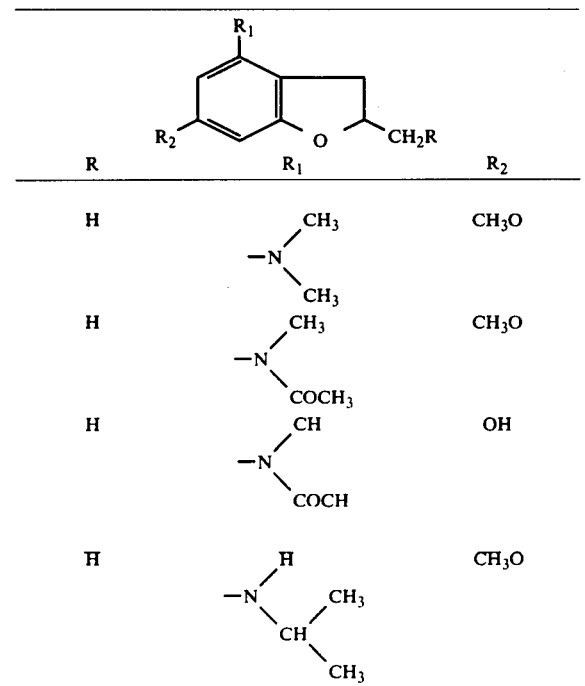

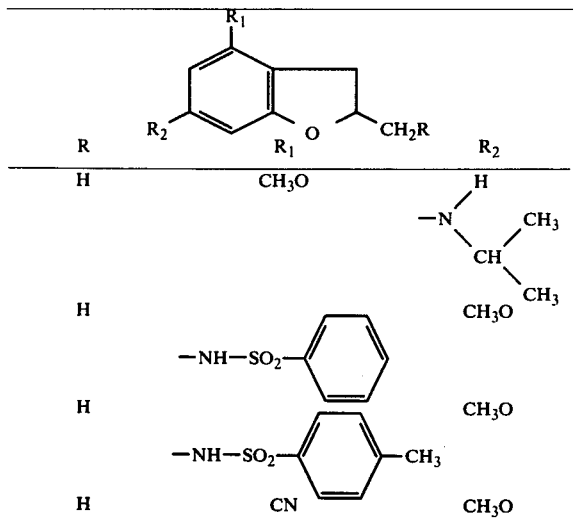

Preparation of the starting material 4-allyl-3-hydroxy-5-methoxy benzoic acid and 2-allyl-3-hydroxy-5-methoxy benzoic acid Starting from 3-hydroxy-5-methoxybenzoic acid methyl ester by reaction with allyl bromide, 3-allyloxy-5-methoxybenzoic acid methyl ester is prepared. B.p. 128°–30° C./0.4 mm Hg. This compound is subjected to allylic rearrangement performed by refluxing in N,N-dimethylaniline under nitrogen atmosphere for about 6 hours. After cooling, the solvent is evaporated and the residue, taken up with ether, is washed with cold diluted HCl and then thoroughly extracted with aqueous 20% NaOH. Separation of the 4-allyl- and 2-allyl-3-hydroxy-5-methoxy-benzoic acids is achieved by fractioned crystallization upon acidification.

1. A 2,4,6-trisubstituted-2,3-dihydro-benzofuran derivative of the following formula

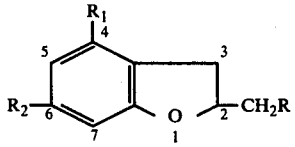

wherein R is selected from hydrogen or methyl; one of $R_1$ and $R_2$ represents hydroxy, $(C_{1-4})$alkoxy or $(C_{2-4})$alkanoyloxy, and the other one is selected from cyano, carboxy, carbo$(C_{1-4})$alkoxy, carbamoyl and a $-NR_3R_4$ group, wherein $R_3$ and $R_4$ independently represent hydrogen, $(C_{1-4})$alkyl, $(C_{2-4})$alkanoyl, carbo$(C_{1-4})$alkoxy, carbobenzyloxy, carbamoyl, mono- and di-$(C_{1-4})$alkylamino-$(C_{1-4})$alkyl, benzenesulfonyl, toluenesulfonyl, $(C_{1-4})$alkylsulfonyl or phenacylsulfonyl: and salts therewith of pharmaceutically acceptable acids.

2. A compound as in claim 1 wherein R stands for hydrogen or methyl, one of $R_1$ and $R_2$ represents hydroxy, $(C_{1-4})$alkoxy or $(C_{2-4})$aliphatic alkanoyloxy and the other one represents the group $-NR_3R_4$ wherein $R_3$ and $R_4$ each independently represents hydrogen or a $(C_{1-4})$alkyl group and salts therewith of pharmaceutically acceptable acids.

3. A compound as in claim 1 wherein R is a hydrogen atom, one of $R_1$ and $R_2$ is a $(C_{1-4})$alkoxy group and the other one is the group $-NR_3R_4$ wherein $R_3$ and $R_4$ each independently represent hydrogen or $(C_{1-4})$alkyl and salts therewith of pharmaceutically acceptable acids.

4. A compound as in claim 1 which is 2,3-dihydro-6-methoxy-N,2-dimethyl-4-benzofuranamine.

* * * * *

UNITED STATES PATENT AND TRADEMARK OFFICE
CERTIFICATE OF CORRECTION

PATENT NO. : 4,143,055
DATED : March 6, 1979
INVENTOR(S) : Emilio Occelli

It is certified that error appears in the above-identified patent and that said Letters Patent are hereby corrected as shown below:

Column 3, line 3, "receovered" should read --recovered--.

Column 6, line 20, "know" should read --known--.

Column 7, line 20, "ether-petroelum" should read --ether-petroleum--.

Column 7, line 58, "oganic" should read --organic--.

Column 8, line 1, "6-ethoxy-2,3-dihydro-N2-dimethyl-4-benzofuranamine" should read -- 6-ethoxy-2,3-dihydro-N,2-dimethyl-4-benzofuranamine--.

Column 11, line 26, "urea" should read --phenacyl-sulfonamine--.

Signed and Sealed this

Thirtieth Day of October 1979

[SEAL]

Attest:

RUTH C. MASON
Attesting Officer

LUTRELLE F. PARKER
Acting Commissioner of Patents and Trademarks